United States Patent [19]

Schwertner

[11] Patent Number: 5,362,649
[45] Date of Patent: Nov. 8, 1994

[54] METHOD FOR CONCENTRATION BASED ANALYSIS OF LIPID FATTY ACIDS AND ITS USE IN DETERMINING THE LIKELIHOOD THAT A PATIENT IS AT RISK FOR CORONARY ARTERY DISEASE

[75] Inventor: Harvey A. Schwertner, San Antonio, Tex.

[73] Assignee: The United States of America as represented by the Secretary of the Air Force, Washington, D.C.

[21] Appl. No.: 19,582

[22] Filed: Feb. 16, 1993

[51] Int. Cl.$^5$ ............................................. G01N 33/92
[52] U.S. Cl. ................................... 436/71; 436/63; 436/161; 436/177
[58] Field of Search ............... 436/71, 63, 811, 161, 436/13, 177; 422/70, 89

[56] References Cited

U.S. PATENT DOCUMENTS

| | | | |
|---|---|---|---|
| 3,751,381 | 8/1973 | Megraw | 252/408 |
| 3,764,556 | 10/1973 | Kuchmak et al. | 252/408 |
| 3,955,925 | 5/1976 | Proksch et al. | 23/230 B |
| 4,239,649 | 12/1980 | Gindler et al. | 252/408 |
| 4,290,774 | 9/1981 | Girgis et al. | 23/230 B |
| 4,868,139 | 9/1989 | Deeg et al. | 436/13 |
| 5,075,101 | 12/1991 | Siguel | 424/9 |
| 5,262,406 | 11/1993 | Vitale | 514/78 |

OTHER PUBLICATIONS

Schwerlner et al. "Clinical Chemistry" 1979 pp. 520–522.

Miettinen et al. "Fatty-Acid Composition of Serum Lipids Predicts Myocardial Infarction", Oct. 1982 pp. 993–995.

Schwertner et al. "Comparison of Lipid Fatty Acids on a Concentration Basis-vs-Weight Percentage Basis in Patients with and without CAD or Diabetes" 1993 pp. 659–663.

Salonen et al. "Serum Fatty Acid, Apolipoproteins, Selenium and Vitamin Antioxidants and the Risk of Death from CAD" Aug. 1985 pp. 226–231.

L. Stoakes, T. Kelly, B. Schieven, D. Harley, M. Ramos, R. Lannigan, D. Groves, and Z. Hussain, Gas–Liquid Chromatographic Analysis of Cellular Fatty Acids for Identification of Gram-Negative Anaerobic Bacilli, Aug. 1991, vol. 29, No. 11, pp. 2636–2638.

David F. Welch, Applications of Cellular Fatty Acid Analysis, Oct. 1991, vol. 4, No. 4, pp. 422–438.

Pirkko Kotilainne, Pentti Huovinen and Erkki Eerola, Application of Gas-Liquid Chromatographic Analysis of Cellular Fatty Acids for Species Identification and Typing of Coagulase-Negative Staphylococci, Nov. 1990, vol. 29, pp. 315–322.

Myron Sasser and Michael D. Wichman, Identification of Microorganisms through use of Gas Chromatography and High-Performance Liquid Chromatography, pp. 111–118.

*Primary Examiner*—James C. Housel
*Assistant Examiner*—N. Bhat
*Attorney, Agent, or Firm*—Fredric L. Sinder; Thomas L. Kundert

[57] ABSTRACT

A new method for determining and reporting lipid fatty acids compositions and its use in diagnosing coronary artery disease and diabetes is disclosed. Adding internal standards, which are true analogs of the fatty acids to be analyzed, to blood serum or plasma samples before performing a gas chromatographic analysis of the fatty acids allows the results of the analysis to be reported in absolute terms as, for example, mg/L, instead of in relative percentages. Reporting the results as absolute concentrations reveals statistically significant differences in levels of various lipid fatty acids between persons having and not having coronary artery disease or diabetes.

7 Claims, No Drawings

METHOD FOR CONCENTRATION BASED ANALYSIS OF LIPID FATTY ACIDS AND ITS USE IN DETERMINING THE LIKELIHOOD THAT A PATIENT IS AT RISK FOR CORONARY ARTERY DISEASE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to methods for determining lipid fatty acid compositions, and more particularly to the use of an improved method for determining lipid fatty acid compositions and its use in diagnosing coronary artery disease and diabetes.

Lipid fatty acids are analyzed in blood serum or plasma, as well as in other physiological fluids and tissues, for a variety of reasons. A primary reason has been in the search for diagnostic predictors for coronary heart disease, diabetes, platelet dysfunction and renal disease. Unfortunately, the serum levels of only a limited number of individual fatty acids have been found statistically significant for coronary artery disease and diabetes.

Saturated fats are known to increase coronary artery disease, or CAD, and polyunsaturated fatty-acids, such as are found in fish and in certain plants, have been shown to decrease the incidence of CAD. For this and other reasons, numerous researchers have investigated and published papers on serum lipid fatty acid composition and heart disease. The results have been largely contradictory. Some studies showed small decreases in cholesterol linoleate, while others showed no change in that fatty acid. Because of these contradictory results, lipid fatty acids have not become part of routine testing.

Current methods for analyzing lipid fatty acids report the fatty acid compositions in relative terms as either percentage by weight of total fatty acids (weight percentages) or percentage by moles of total moles of all fatty acids (mole percentages). With such methods, changes in each individual fatty acid has an influence on the relative percentages of the other fatty acids. As a result, exact information on the fatty acid compositions are not obtained and the information is difficult to interpret.

Thus it is seen that there is a need for improved methods for analyzing and reporting fatty acid compositions in blood serum or plasma that will better reveal the expected, but previously undiscovered, relationships between fatty acid compositions and heart and other diseases.

It is, therefore, a principal object of the present invention to provide an improved method for analyzing and reporting fatty acid compositions, particularly in blood serum or plasma.

Another principal object of the present invention is to provide new statistically significant risk factors for coronary artery disease and for diabetes.

It is a feature of the present invention that it permits quantification of individual fatty acids in absolute terms, such as mg/L, rather than in relative terms such as percentages.

It is another feature of the present invention that it uses conventional laboratory equipment and supplies.

It is an advantage of the present invention that it provides greater diagnostic accuracy and sensitivity than prior art methods for determining lipid fatty acid compositions.

It is another advantage of the present invention that its concentration-based results can be more easily interpreted in metabolic, dietary and therapeutic terms than existing methods of reporting results.

It is a further advantage of the present invention that its improved method of analyzing and reporting fatty acid compositions will improve other areas where analysis of fatty acid compositions are used, such as in microbial identification systems, and for analyzing food products, such as dairy, meat, fish and seed oils, for accurate reporting and labeling of the saturated and unsaturated fatty acid content of foods and food products.

It is yet another advantage of the present invention that the increased knowledge of free acid concentrations will lead to better diagnosis and treatment of many diseases.

These and other objects, features and advantages of the present invention will become apparent as the description of certain representative embodiments proceeds.

SUMMARY OF THE INVENTION

The present invention provides new methods for analyzing and reporting lipid fatty acid compositions, particularly in blood serum or plasma, and new individual lipid fatty acid risk factors for heart disease and for diabetes. The unique discovery of the present invention is that the use of internal standards, which are true analogs of a class of lipid fatty acids to be analyzed by gas-liquid chromatographic (or other analytical) methods, permits reporting fatty acid concentrations in absolute, rather than percentage, terms, and that the use of that improved method reveals new statistically significant risk factors for heart disease and for diabetes.

Accordingly, the present invention is directed to a method for analyzing lipid fatty acid compositions in a sample of blood serum, comprising the steps of adding a known amount of an internal standard to a known amount of the sample, wherein the internal standard is a true analog of a class of lipid fatty acids to be analyzed, extracting the lipids from the sample, separating the lipid fractions, identifying the individual fatty acids, and reporting the concentration of the individual fatty acids as weight of each individual fatty acid per amount of sample. Alternatively, the concentration of the individual fatty acids may be reported as moles of each individual fatty acid per amount of sample. Any chromatographic method may be used for the analysis and, in that case, the concentrations to be reported may be determined by reporting the peak areas of the individual fatty acids including the area of the fatty acid component of the internal standard and comparing the areas of the individual fatty acids to the weight and area of the fatty acid component of the internal standard and calculating the weight of the individual fatty acids per amount of the sample. The internal standard for the class of lipid fatty acids known as serum cholesterol ester fatty acids may be cholesteryl heptadecanoate. The internal standard for the class of lipid fatty acids known as serum phospholipid fatty acids may be phosphatidylcholine diheptadecanoyl.

The present invention is also directed to a method for determining the likelihood that a patient is at risk for coronary artery disease, comprising the steps of measuring the patient's serum cholesterol ester fatty acid concentration of a fatty acid selected from a group consisting of palmitic acid, oleic acid, linoleic acid, arachidonic acid, eicosapentaenoic acid and docosahexaenoic acid, comparing the measured concentration to a threshold level for serum cholesterol ester fatty acid concentration for that fatty acid, and determining from the comparison the likelihood that the patient is at risk for coronary artery disease. The threshold level for each fatty acid listed in the group may be, respectively, 823, 1366, 4358, 688, 67 and 40 milligrams per liter of serum.

The present invention is also directed to a method for determining the likelihood that a patient is at risk for coronary artery disease, comprising the steps of measuring the patient's serum phospholipid fatty acid concentration of a fatty acid selected from a group consisting of oleic acid, linoleic acid, eicosatrienoic acid and arachidonic acid, comparing the measured concentration to a threshold level for serum phospholipid fatty acid concentration for that fatty acid, and determining from the comparison the likelihood that the patient is at risk for coronary artery disease. The threshold level for each fatty acid listed in the group may be, respectively, 1006, 1887, 266 and 1017 milligrams per liter of serum.

The present invention is further directed to a method for determining the likelihood that a patient is at risk for coronary artery disease, comprising the steps of measuring the patient's total serum fatty acid concentration, comparing the measured concentration to a threshold level for total serum fatty acid concentration, and determining from the comparison the likelihood that the patient is at risk for coronary artery disease.

The present invention is yet also directed to a method for determining the likelihood that a patient is at risk for diabetes, comprising the steps of measuring the patient's serum free fatty acid concentration of a fatty acid selected from a group consisting of oleic acid and arachidonic acid, comparing the measured concentration to a threshold level for serum free fatty acid concentration for that fatty acid, and determining from the comparison the likelihood that the patient is at risk for diabetes. The threshold level for each fatty acid listed in the group may be, respectively, 1239.5 and 42.2 milligrams per liter of serum.

The present invention is yet further directed to a method for determining the likelihood that a patient is at risk for diabetes, comprising the steps of measuring the patient's total serum fatty acid concentration, comparing the measured concentration to a threshold level for total serum fatty acid concentration, and determining from the comparison the likelihood that the patient is at risk for diabetes.

DETAILED DESCRIPTION

Serum lipid fatty acid compositions have been determined in a variety of diseases and disorders, including coronary artery disease, diabetes, platelet dysfunction and renal disease. The effects of diet and age on serum lipid fatty acids have also been determined and a large number of studies have been published on this subject. An examination of those studies reveals that nearly all of the results were reported on a relative percentage basis. Further, none of those studies have examined the validity of reporting fatty acid compositions on a percentage basis versus expressing them in absolute terms such as mg/L or mmole/L. This is somewhat surprising in that when the results are presented on a relative percentage basis, the percentage of each fatty acid is influenced by changes in the other fatty acids. On the other hand, if the fatty acid results were reported as absolute concentrations, changes in fatty acids would be independent of each other.

The present invention demonstrates that fatty acid results expressed on a weight percentage basis convey different information from those expressed as concentrations. The term "concentration" is used in this description to mean absolute concentrations, while the term "composition" is used to mean either relative or absolute means for reporting results. Similarly, the term "analysis" is used in its broader sense to generally refer to the entire process, and not merely to the use of gas-liquid chromatographic equipment.

The serum cholesterol ester and the phospholipid fatty acid compositions of individuals with coronary artery disease were determined and the results reported for the first time on an absolute concentration basis. These results were compared to those of individuals without coronary artery disease. The composition of free fatty acids in patients with and without diabetes was also compared. The following description of several studies discloses the method used to, first, extract the lipids, second, separate the lipid classes and, finally, identify and report the individual fatty acids. The method employs appropriate internal standards which permit the quantitative analysis of individual serum lipid fatty acids.

STUDY METHODS

Parts of the described study are similar to a study described in copending application Ser. No. 07/968,881, "Serum Bilirubin and Liver Function Tests as Risk Predictors for Coronary Artery Disease," filed Oct. 30, 1992 by the same inventor, which is incorporated into this description as though fully rewritten.

Patients

The first study group consisted of 30 male patients who had undergone cardiac catheterization and coronary angiography for evaluation of suspected coronary artery disease. Eighteen of the patients had 50 percent narrowing of one or more vessels and were considered to have significant CAD. The other 12 patients had normal arteriograms. The ages of the CAD and non-CAD groups were $47 \pm 5$ and $44 \pm 6$ ($\pm SD$) years. The second study group consisted of seven patients with uncontrolled adult-onset type diabetes and five patients without clinical evidence of diabetes. The average age of the patients in the study group was $55 \pm 12$ ($\pm SD$) years. Blood samples in the first group were obtained after a 12-hour overnight fast on the day after admission but before cardiovascular testing. The blood samples used in the diabetes study group were all non-fasting samples. The fatty acid results in the diabetes study group were taken from an earlier study which used a slightly different analytical method.

Reagents and Supplies

Boron-trifluoride-methanol, rhodamine 6G, and the internal standards were obtained from Sigma Chemical Company, St. Louis, Mo. The thin-layer chromatographic plates, LK5DF, 250$\mu$, were obtained from Whatman Chemical Separations, Inc., Clifton, N.J. All solvents were "pesticide grade" or "glass-distilled HPLC grade."

Internal Standards

The internal standards used in this study, cholesteryl heptadecanoate and phosphatidylcholine diheptadecanoyl, were prepared in chloroform-methanol (2:1, v/v) at a concentration of 1 mg/ml. Cholesteryl heptadecanoate is a true analog of the cholesterol esters, and phosphatidylcholine diheptadecanoyl is a true analog of the phospholipid fatty acids. They differ from the fatty acids sought to be analyzed primarily in that they have carbon chains having an odd number of carbon atoms. They are generally synthetically produced. Other fatty acids used to prepare internal standards can be derived from plants or microbial sources. Animal serum lipid fatty acids generally have carbon chains with an even number of carbon atoms so that the odd number carbon atom fatty acids from the internal standards are easily distinguishable from the even number carbon atom fatty acids extracted and separated from the serum lipids.

Extraction

To analyze the serum cholesterol ester and phospholipid fatty acids, 1 mL of serum was added to separate 25×150 mm screw-capped culture tubes along with 1 mL of the cholesterol ester and phospholipid internal standards, 100 μL of butylated hydroxy-toluene (BHT, 10 mg/ml in methanol), 15 mL of chloroform-methanol (2:1 by volume) and 5 mL of 0.2M sodium dihydrogen phosphate buffer. The samples were mixed for 10 minutes on an Eberbach shaker and then centrifuged (2000 g for 2 min) to separate the organic and aqueous phases. Using a 10 mL volumetric pipette, about 9 mL of each chloroform (lower) phase was transferred to 16×125 mm culture tube. The samples were then placed in a 65° C. heating block and the organic solvent evaporated in a stream of nitrogen. The lipids were redissolved in 150 μL of chloroform-methanol (2:1) and either stored in a freezer or applied directly to the thin-layer chromatographic (TLC) plates.

Separation

Thin-layer Chromatography

The lipids were applied to the TLC plates with glass capillary tubes. The lipid classes were then separated with n-hexane-ethyl ether-acetic acid-BHT (60 mL 95:5:1:0.1, v/v/v/v). The plates were sprayed with rhodamine 6G (0.1% in methanol) and the lipid classes were detected under long wavelength ultraviolet light. The lipid fractions were scraped with a sharpened spatula onto weighing paper and then transferred along with 20 μL of BHT into separate 16×125 mm screw-capped tubes.

Hydrolysis and Esterification

To hydrolyze the cholesterol ester and the phospholipid fractions, 2 mL of methanol KOH, 0.5 mol/L, was added and the samples heated for 20 minutes at 95° C. The samples were vortex-mixed (1 min) before heating, after 10 min of heating, and again after 20 min of heating. After hydrolysis, the tubes were allowed to cool, then 2 mL of boron-trifluoride-methanol (140 g/L) was added and the samples heated for 5 minutes at 95° C. To extract the fatty acid methyl esters, 5 mL of n-hexane was added to each tube and the samples shook on an Eberbach shaker for 5 min. The hexane phase was then transferred with a Pasteur pipet to separate 16×125 mm screw-capped tubes. After adding 5 mL of deionized water, the tubes were shaken for 5 minutes, then centrifuged to separate the phases. The hexane phase was again transferred to separate 16×125 mm screw-capped tubes. The samples were then either stored at 4° C. or were evaporated and reconstituted in 300 μl of hexane for gas-chromatographic analysis.

Identification

Instrument

For the identification part of the analysis, a Varian gas-chromatograph equipped with a hydrogen flame ionization detector was used with a 2 m×2 mm (i.d.) 12% DEGS on Chromosorb W(HD), 80/100 mesh column. The analysis of the fatty acid methyl esters were performed under isothermal conditions at 164° C.

Statistics

The within-day coefficient of variation (CV) was based on an analysis of 10 samples with all the samples being extracted and analyzed during the same day. The between-day CV was based on an analysis of single samples on 10 separate days. The within-day and between-day coefficients of variation were 4.5 percent and 7.8 percent, respectively, and represented the average phospholipid and cholesterol ester concentrations. The Students t-test with pooled variance estimates was used for the statistical analysis. Significance levels were determined using 2-tail probability values.

Reporting

The use of internal standards corrects for incomplete extractions, losses during thin-layer chromatography and incomplete hydrolysis and esterification. Because the starting amount of the internal standards is known, what must have been the starting amount of the other fatty acids can be determined by comparison with the amount of remaining fatty acid component of the internal standards. Quantification is achieved by comparing peak areas or peak heights of a known amount of the internal standard to the peak area, or height, of the sample lipid fatty acids being analyzed. This method is the same for any chromatographic method.

The weight concentration and weight percentages of the cholesterol ester fatty acids are given in Table I. When the results were expressed as absolute weight concentrations, six fatty acids (palmitic, oleic, linoleic, arachidonic, eicosapentaenoic, and docosahexaenoic acid) were found to be significantly higher in the group with CAD than in the group without CAD. When the results were expressed on a weight percentage basis, there were no statistical differences in the fatty acid compositions of the two groups. The concentrations of all of the cholesterol ester fatty acids, except linolenic acid and docosapentaenoic acid, were higher in the CAD group than in the non-CAD group. On a weight percentage basis, half were higher and half were lower but none were found to be statistically different. The total fatty acid concentrations were also higher in the CAD group than in the non-CAD groups.

TABLE I

SERUM CHOLESTEROL ESTER FATTY ACID COMPOSITION

| FATTY ACID DESIGNATION | $C_{16:0}$ | $C_{18:0}$ | $C_{18:1}$ | $C_{18:2}$ | $C_{18:3}$ | $C_{20:3}$ | $C_{20:4}$ | $C_{20:5}$ | $C_{22:5}$ | $C_{22:6}$ | TOTAL |
|---|---|---|---|---|---|---|---|---|---|---|---|
| CONCENTRATION (mg/L) | | | | | | | | | | | |
| *No-CAD* | | | | | | | | | | | |
| Mean | 603 | 6 | 961 | 2969 | 16 | 28 | 427 | 33 | 3.4 | 22 | 5066 |
| S.D. | 84 | 12 | 209 | 521 | 16 | 12 | 76 | 20 | 6.6 | 8 | 823 |
| *≧50% CAD* | | | | | | | | | | | |
| Mean | 823 | 13 | 1366 | 4358 | 17 | 33 | 688 | 67 | 3.1 | 40 | 7407 |
| S.D. | 270 | 21 | 373 | 1115 | 17 | 21 | 173 | 48 | 8.0 | 28 | 1558 |
| T-VALUES** | −2.73 | −1.15 | −3.41 | −4.02 | −0.25 | −.73 | −4.90 | −2.36 | 0.13 | −2.13 | −4.76 |
| DF | 28 | 28 | 28 | 28 | 28 | 28 | 28 | 28 | 28 | 28 | 28 |
| P | .011 | .26 | .002 | .000 | .80 | .47 | .000 | .025 | .898 | .042 | .000 |
| WEIGHT PERCENT (%) | | | | | | | | | | | |
| *No-CAD* | | | | | | | | | | | |
| Mean | 12.0 | 0.1 | 18.9 | 58.6 | 0.3 | 0.5 | 8.5 | 0.6 | 0.08 | 0.4 | |
| S.D. | 1.0 | 0.2 | 2.7 | 3.0 | 0.3 | 0.2 | 0.1 | 0.3 | 0.1 | 0.1 | |
| *≧50% CAD* | | | | | | | | | | | |
| Mean | 11.3 | 0.2 | 18.4 | 58.6 | 0.2 | 0.4 | 9.4 | 0.9 | 0.04 | 0.5 | |
| S.D. | 3.1 | 0.3 | 2.5 | 5.0 | 0.2 | 0.3 | 2.2 | 0.6 | 0.1 | 0.4 | |
| T-VALUES** | 0.67 | −0.97 | 0.62 | 0.02 | 0.68 | 1.13 | −1.42 | −1.41 | 0.86 | −0.97 | |
| DF | 28 | 28 | 28 | 28 | 28 | 28 | 28 | 28 | 28 | 28 | |
| P | .51 | .34 | .54 | .99 | .50 | .27 | .17 | .17 | .40 | .34 | |

*The concentrations of individual fatty acids can be converted to mmoles/L by using the following molecular weights:
$C_{16:0}$, palmitic acid (256.5); $C_{18:0}$, stearic acid (284.5); $C_{18:1}$, oleic acid (282.5); $C_{18:2}$, linoleic acid (280.5); $C_{18:3}$, linolenic acid (278.5); $C_{20:3}$, eicosatrienoic acid (306.5); $C_{20:4}$, arachidonic acid (304.5); $C_{20:5}$, eicosapentaenoic acid (302.5); $C_{22:5}$, docosapentaenoic acid (330.5); $C_{22:6}$, docosahexaenoic acid (328.5).
**The sum of the T-values for weight and weight percent calculations were 21.81 an 7.75, respectively.

The concentrations and weight percentages of phospholipid fatty acids for individuals with and without CAD are shown in Table II. The concentrations of seven fatty acids (palmitic, stearic, oleic, linoleic, eicosatrienoic, arachidonic and eicosapentaenoic acid) differed in the CAD and non-CAD groups. All of these fatty acids, except for eicosapentaenoic acid, were higher in the CAD group than in the non-CAD group. When the results were expressed on a relative percentage basis, four fatty acids were found to differ statistically: palmitic, stearic, eicosapentaenoic, and docosahexaenoic acid. Two of the fatty acids were increased in the CAD group and two were lower in relative terms.

TABLE II

SERUM PHOSPHOLIPID FATTY ACID COMPOSITION

| FATTY ACID DESIGNATION | $C_{16:0}$ | $C_{18:0}$ | $C_{18:1}$ | $C_{18:2}$ | $C_{18:3}$ | $C_{20:3}$ | $C_{20:4}$ | $C_{20:5}$ | $C_{22:5}$ | $C_{22:6}$ | TOTAL |
|---|---|---|---|---|---|---|---|---|---|---|---|
| CONCENTRATION (mg/L) | | | | | | | | | | | |
| *No-CAD* | | | | | | | | | | | |
| Mean | 1485 | 688 | 761 | 1421 | 48 | 202 | 718 | 106 | 80 | 201 | 5710 |
| S.D. | 212 | 111 | 87 | 196 | 66 | 36 | 101 | 59 | 19 | 47 | 577 |
| *≧50% CAD* | | | | | | | | | | | |
| Mean | 2147 | 1131 | 1006 | 1887 | 22 | 266 | 1017 | 61 | 77 | 247 | 7859 |
| S.D. | 458 | 277 | 215 | 543 | 27 | 102 | 222 | 39 | 19 | 106 | 1648 |
| T-VALUES** | −4.7 | −5.24 | −3.73 | −2.84 | 1.5 | −2.10 | −4.35 | 2.54 | 0.50 | −1.38 | −4.32 |
| DF | 28 | 28 | 28 | 28 | 28 | 28 | 28 | 28 | 28 | 28 | 28 |
| P | .000 | .000 | .001 | .008 | .144 | .045 | .000 | .017 | .619 | .177 | .000 |
| WEIGHT PERCENT (%) | | | | | | | | | | | |
| *No-CAD* | | | | | | | | | | | |
| Mean | 25.9 | 12.0 | 13.4 | 24.9 | 0.8 | 3.6 | 12.6 | 1.9 | 1.4 | 3.6 | |
| S.D. | 1.7 | 1.0 | 1.2 | 2.2 | 1.2 | 0.6 | 1.3 | 1.1 | 0.4 | 1.0 | |
| *≧50% CAD* | | | | | | | | | | | |
| Mean | 27.3 | 14.4 | 12.9 | 23.8 | 0.3 | 3.3 | 13.1 | 0.8 | 0.9 | 3.2 | |
| S.D. | 1.6 | 1.3 | 1.6 | 3.2 | 0.4 | 0.7 | 2.3 | 0.5 | 0.2 | 1.3 | |
| T-VALUES** | −2.31 | −5.29 | 0.92 | 0.98 | 1.87 | 0.91 | −0.70 | 3.90 | 4.32 | 0.92 | |
| DF | 28 | 28 | 28 | 28 | 28 | 28 | 28 | 28 | 28 | 28 | |
| P | .029 | .000 | .363 | .337 | .072 | .373 | .488 | .001 | .000 | .365 | |

*To convert mg/L to mmoles/L, use molecular weights given in footnote to Table I.
**The sum of the T-values for weight and weight percent calculations were 28.88 and 22.12, respectively.

The concentration and weight percentage of the serum free fatty acids in diabetics and non-diabetics are given in Table III. On a concentration basis, five fatty acids were statistically higher in the diabetic group than in the non-diabetic group, palmitic, stearic, oleic, linoleic and arachidonic acid. When the results were expressed on a weight percent basis, only palmitic, stearic, and linoleic acids were statistically significant.

TABLE III

| SERUM FREE FATTY ACID COMPOSITION | | | | | | | |
|---|---|---|---|---|---|---|---|
| FATTY ACID DESIGNATION | $C_{16:0}$ | $C_{18:0}$ | $C_{18:1}$ | $C_{18:2}$ | $C_{20:3}$ | $C_{20:4}$ | TOTAL |
| CONCENTRATION (mg/L) | | | | | | | |
| *No-DIABETES* | | | | | | | |
| Mean | 200.2 | 75.9 | 267.7 | 90.3 | 1.4 | 13.7 | 649.3 |
| S.D. | 36.6 | 35.9 | 92.5 | 29.2 | 1.2 | 4.4 | 135.4 |
| *DIABETES* | | | | | | | |
| Mean | 667.4 | 207.0 | 1239.5 | 538.5 | 10.0 | 42.2 | 2704.7 |
| S.D. | 307.9 | 115.6 | 779.8 | 90.3 | 9.6 | 28.9 | 1454.8 |
| T-VALUES** | −3.33 | −2.42 | −2.73 | −3.82 | −1.96 | −2.16 | −3.11 |
| DF | 10 | 10 | 10 | 10 | 10 | 10 | 10 |
| P | .008 | .036 | .021 | .003 | .079 | .050 | .011 |
| WEIGHT PERCENT (%) | | | | | | | |
| *No-DIABETES* | | | | | | | |
| Mean | 31.1 | 12.0 | 40.7 | 13.9 | 0.2 | 2.2 | |
| S.D. | 2.8 | 5.4 | 7.6 | 3.6 | 0.2 | 0.7 | |
| *DIABETES* | | | | | | | |
| Mean | 25.2 | 7.5 | 44.8 | 20.6 | 0.4 | 1.6 | |
| S.D. | 2.6 | 1.1 | 3.4 | 3.8 | 0.3 | 0.8 | |
| T-VALUES** | 3.73 | 2.19 | −1.29 | −3.06 | −0.82 | 1.2 | |
| DF | 10 | 10 | 10 | 10 | 10 | 10 | |
| P | .004 | .053 | .227 | .012 | .433 | .257 | |

*To convert mg/L to mmoles/L, use molecular weights given in footnote to Table I.
**The sum of the T-values for weight and weight percent calculations were 16.42 and 12.29, respectively.

As can be seen in the tables, the sum of the T-values were higher for the concentration-based calculations than for the weight percent calculations.

Fatty acid results were also calculated on a molar basis and on a mole percentage basis. The differences between these two methods of calculation were identical or nearly identical to the differences found between results calculated on a weight concentration basis and on a weight percentage basis. In addition, T-values for results calculated on a molar basis were found to be identical to those calculated on a concentration basis. Because of differences in the molecular weights of the individual fatty acids, T-values of results calculated on a mole percentage basis differed slightly from those calculated on a weight percentage basis.

The study shows that impressions about lipid fatty acid compositions are different when results are expressed as absolute concentrations rather than on a weight percentage basis. Most of the methods used to study lipid fatty acids in coronary heart disease, diabetes and platelet dysfunction have been based on methods employing weight percentage calculations. Likewise, most, but not all, of the analytical methods developed for fatty acid analysis have been based on weight percentage calculations.

The advantages of using concentration-based analysis versus weight percentage analysis are clear. With concentration-based results, the amounts of individual fatty acids are independent of each other. However, when weight percentage calculations are used, each fatty acid being analyzed has an influence on the relative percentage of the other fatty acids. Another advantage of concentration-based analysis is that the results can be more easily interpreted in metabolic and in therapeutic terms. As an example, cholesterol linoleate is widely believed to decrease in patients with coronary heart disease. Such decreases, however, represent decreases only in relative terms. The present invention shows that linoleate is actually in a higher concentration in individuals with coronary artery disease then in those without coronary artery disease.

Fatty acid analyses are also widely used to identify bacteria and fungi in the laboratory by their unique fatty acid compositions. These methods rely exclusively on weight percentage results. Those with skill in the art will readily see that concentration results will further improve the sensitivity and specificity of those methods. Because volume measurements may not be applicable in all cases, the fatty acid concentrations would have to be related to the number of microorganisms, the amount of membrane protein, the amount of DNA, or some other unit of measure.

The method used in this study permits accurate and relatively precise measurement of serum or plasma lipid fatty acid concentrations. The internal standards used, phosphatidylcholine diheptadecanoyl and cholesteryl heptadecanoate, correct for incomplete extractions, losses during thin-layer chromatography and incomplete hydrolysis and esterification. A number of other candidate internal standards have been evaluated with good results, including phosphatidylcholine dipentadecanoyl and dibehenoyl; and, cholesterol pentadecanoate, arachidate, eicosenoate, behenate, erucate, lignocerate and nervonate. Those with skill in the art of the invention will readily see that the choice of a specific internal standard used will depend on the type of physiological fluid or tissue being analyzed. The type of internal standard will also depend on the lipids being analyzed and their specific fatty acids. Those with skill in the art will readily see that the choice of internal standard is also governed by the type of chromatographic stationary phase and the chromatographic operating conditions. The choice of internal standards may include radioactive analogs, deuterated analogs or various fatty acid isomers. The latter would include fatty acids with double bonds in different positions of the carbon chain or may include branch chain fatty acids. If the analysis is performed by gas-chromatography, mass-spectrometry, or high-performance liquid-chromatography, various fluorescent, ultraviolet absorbing internal standards or deuterated internal standards would be used.

The present invention shows that future studies should be performed on both concentration (mg/L or mmol/L) and weight percentage bases and further comparisons made. Concentration-based results may not always be superior to weight percentage results, but can always be more readily interpreted in metabolic, dietary and therapeutic terms.

A particularly useful result of the present invention is that the mean and standard deviations of many of the lipid fatty acids in the >=50% CAD group are completely separate from those of the group without CAD, that is, there is little or no overlap of the standard deviations. This result leads to improved disease prediction.

Those with skill in the art of the invention will readily see that specific lipid fatty acid concentrations may in the future be combined, divided, assigned different weights, or expanded in logarithmic terms using various multi-factorial formulas to discover other statistically significant indicators.

Those with skill in the art will also readily see that the steps described in the claims can be performed in whole or in part by a computer program, either in a stand-alone computer or as part of an automated analysis instrument, such as an automated gas-liquid chromatographic system, gas chromatographic mass-spectrometer or high-performance liquid chromatograph.

Those with skill in the art of the invention will also see that in the future a kit may be designed to determine total phospholipid fatty acids in serum by means other than chromatography, such as enzymatic testing or by immunologic assay.

The disclosed new method for determining serum lipid fatty acid compositions successfully demonstrates the use of absolute concentration results for diagnosis of disease. Although the disclosed methods are specialized, their teachings will find application in other areas where diagnostically significant, or other useful, information is currently lost or hidden because of either the method by which analysis is performed, the manner in which it is reported, or both.

The terminology used in the claims refers in the preambles to a sample of blood serum. The use of the term "sample" in the body of the claims, however, is understood to refer to a sample of any biological or non-biological material, natural or synthetic, which may contain lipid fatty acids. Some examples include dairy products, meat products, fish, yeast, plants, seed oils and mineral oils. The term "concentration" is limited to mean by absolute weight per unit of some amount (such as volume) or by absolute moles per unit of some amount. The term "amount" is understood to refer to any unit of sample, such as volume, number of cells or weight. This terminology allows for expressing concentrations in such other terms as weight per weight basis, weight of fatty acid per weight of protein or DNA. Concentration might also be expressed on a weight per number basis, such as weight of fatty acid per number of bacteria, per number of platelets or per number of cells.

It is understood that various modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

I claim:

1. A method for identifying and quantifying lipid fatty acid compositions in a sample of blood serum, comprising the steps of:
   (a) adding a known amount of an internal standard to a known amount of the sample, wherein the internal standard is a true analog of a class of lipid fatty acids to be analyzed;
   (b) after adding the internal standard, extracting the lipids from the sample;
   (c) separating the lipid fractions from each other;
   (d) identifying the individual fatty acids;
   (e) reporting the concentration of the individual fatty acids as weight of each individual fatty acid per amount of sample.

2. The method for analyzing lipid fatty acid compositions according to claim 1, wherein step (e) is characterized as reporting the concentration of the individual fatty acids as moles of each individual fatty acid per amount of sample.

3. The method for analyzing lipid fatty acid compositions according to claim 1, wherein any chromatographic method is used for the analysis and further comprising:
   (a) in step (d), reporting the peak areas of the individual fatty acids including the area of the fatty acid component of the internal standard; and,
   (b) in step (e), comparing the areas of the individual fatty acids to the weight and area of the fatty acid component of the internal standard and calculating the weight of the individual fatty acids per amount of the sample.

4. The method for analyzing lipid fatty acid compositions according to claim 1, wherein the internal standard for the class of lipid fatty acids known as serum cholesterol ester fatty acids is cholesteryl heptadecanoate.

5. The method for analyzing lipid fatty acid compositions according to claim 1, wherein the internal standard for the class of lipid fatty acids known as serum phospholipid fatty acids is phosphatidylcholine diheptadecanoyl.

6. A method for determining the likelihood that a patient is at risk for coronary artery disease, comprising the steps of:
   (a) measuring the patient's serum cholesterol ester fatty acid concentration of a fatty acid selected from a group consisting of palmitic acid, oleic acid, linoleic acid, arachidonic acid, eicosapentaenoic acid and docosahexaenoic acid;
   (b) comparing the measured concentration to a threshold level for serum cholesterol ester fatty acid concentration for that fatty acid wherein the threshold level for each fatty acid listed in the group is, respectively, 823, 1366, 4358, 688, 67 and 40 milligrams per liter of serum; and,
   (c) determining from the comparison the likelihood that the patient is at risk for coronary artery disease.

7. A method for determining the likelihood that a patient is at risk for coronary artery disease, comprising the steps of:
   (a) measuring the patient's serum phospholipid fatty acid concentration of a fatty acid selected from a group consisting of oleic acid, linoleic acid, eicosatrienoic acid and arachidonic acid;
   (b) comparing the measured concentration to a threshold level for serum phospholipid fatty acid concentration for that fatty acid wherein the threshold level for each fatty acid listed in the group is, respectively, 1006, 1887, 266 and 1017 milligrams per liter of serum; and,
   (c) determining from the comparison the likelihood that the patient is at risk for coronary artery disease.

* * * * *